(12) United States Patent
Zeng et al.

(10) Patent No.: US 11,062,490 B2
(45) Date of Patent: Jul. 13, 2021

(54) REINFORCEMENT LEARNING FOR ONLINE SAMPLING TRAJECTORY OPTIMIZATION FOR MAGNETIC RESONANCE IMAGING

(71) Applicant: The Board of Trustees of the Leland Stanford Junior University, Stanford, CA (US)

(72) Inventors: David Y. Zeng, San Francisco, CA (US); Shreyas S. Vasanawala, Stanford, CA (US); Joseph Yitan Cheng, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 147 days.

(21) Appl. No.: 16/654,368

(22) Filed: Oct. 16, 2019

(65) Prior Publication Data
US 2020/0134887 A1    Apr. 30, 2020

Related U.S. Application Data

(60) Provisional application No. 62/750,342, filed on Oct. 25, 2018.

(51) Int. Cl.
*G06K 9/00* (2006.01)
*G06T 11/00* (2006.01)
(Continued)

(52) U.S. Cl.
CPC ............ *G06T 11/006* (2013.01); *A61B 5/055* (2013.01); *G01R 33/5608* (2013.01); *G06N 3/04* (2013.01);
(Continued)

(58) Field of Classification Search
CPC ......... G06T 11/006; G06T 2207/20081; G06T 2207/10088; G06T 2207/20084;
(Continued)

(56) References Cited

U.S. PATENT DOCUMENTS

| 8,717,020 B2 | 5/2014 | Griswold |
| 2017/0053402 A1* | 2/2017 | Migukin ............... G06T 7/0012 |

(Continued)

OTHER PUBLICATIONS

Hessel et al., Rainbow: Combining Improvements in Deep Reinforcement Learning. arXiv:1710.02298v1 [cs. AI] Oct. 6, 2017.
(Continued)

*Primary Examiner* — Charlotte M Baker
(74) *Attorney, Agent, or Firm* — Lumen Patent Firm (57) ABSTRACT

A magnetic resonance imaging scan performs an MRI acquisition using an undersampling pattern to produce undersampled k-space data; adds the undersampled k-space data to aggregate undersampled k-space data for the scan; reconstructs an image from the aggregate undersampled k-space data; updates the undersampling pattern from the reconstructed image and aggregate undersampled k-space data using a deep reinforcement learning technique defined by an environment, reward, and agent, where the environment comprises an MRI reconstruction technique, where the reward comprises an image quality metric, and where the agent comprises a deep convolutional neural network and fully connected layers; and repeats these steps to produce a final reconstructed MRI image for the scan.

6 Claims, 8 Drawing Sheets

(51) Int. Cl.
  *G06N 3/08* (2006.01)
  *G06N 3/04* (2006.01)
  *A61B 5/055* (2006.01)
  *G01R 33/56* (2006.01)

(52) U.S. Cl.
  CPC ...... G06N 3/08 (2013.01); *G06T 2207/10088* (2013.01); *G06T 2207/20081* (2013.01); *G06T 2207/20084* (2013.01)

(58) Field of Classification Search
  CPC ............ G06N 3/08; G06N 3/04; G06N 7/005; G06N 3/0454; G06N 3/088; G06N 3/006; G01R 33/5608; G01R 33/561; G01R 33/4818; A61B 5/055
  USPC .................................................. 382/128, 131
  See application file for complete search history.

(56) References Cited

U.S. PATENT DOCUMENTS

| | | | |
|---|---|---|---|
| 2019/0147589 A1* | 5/2019 | Zhou | G06T 7/0012 382/131 |
| 2019/0353741 A1* | 11/2019 | Bolster, Jr. | G01R 33/56509 |
| 2020/0103483 A1* | 4/2020 | Hardy | G06T 7/0012 |

OTHER PUBLICATIONS

Mnih et al., Human-level control through deep reinforcement learning, Nature, vol. 518, pp. 529-533 (Feb. 26, 2015).
Knoll et al., Adapted random sampling patterns for accelerated MRI, Magnetic Resonance Materials in Physics, Biology and Medicine, Feb. 2011, vol. 24, Issue 1, pp. 43-50.
Zhu et al., AUTOmated pulse SEQuence generation (AUTOSEQ) and neural network decoding for fast quantitative MR parameter measurement, Proc. Intl. Soc. Mag. Reson. Med. 27 (2019).

* cited by examiner

REINFORCEMENT LEARNING FOR ONLINE SAMPLING TRAJECTORY OPTIMIZATION FOR MAGNETIC RESONANCE IMAGING

CROSS-REFERENCE TO RELATED APPLICATIONS

This application claims priority from U.S. Provisional Patent Application 62/750,342 filed Oct. 25, 2018, which is incorporated herein by reference.

STATEMENT REGARDING FEDERALLY SPONSORED RESEARCH OR DEVELOPMENT

This invention was made with Government support under contract EB009690 and HL127039 awarded by the National Institutes of Health. The Government has certain rights in the invention.

FIELD OF THE INVENTION

The present invention relates generally to magnetic resonance imaging (MRI) techniques. More specifically, it relates to methods for MRI using undersampling.

BACKGROUND OF THE INVENTION

Magnetic resonance imaging (MRI) is an important medical imaging modality but MRI scans can be slow to acquire complete data for basic image reconstruction techniques. MRI acquires data in the Fourier domain over several readouts and requires several minutes per scan to acquire enough data to satisfy Shannon-Nyquist sampling rates. For example, in Cartesian sampling, one row of the Cartesian matrix is sampled per readout and this must be repeated for all rows.

To accelerate imaging, less data can be acquired in a process known as undersampling. Using non-linear reconstruction techniques such as compressed sensing and deep learning, clinically-useful images can be recovered from the undersampled data. However, an unsolved problem is how to optimally choose the undersampling pattern, i.e., which data points to acquire when undersampling, as the best pattern can depend on many factors including anatomy, reconstruction technique, and image quality metric used to define optimality.

BRIEF SUMMARY OF THE INVENTION

Although there have been prior attempts to find an optimal undersampling pattern, they have only used prior data. These existing techniques for undersampling are thus predetermined, not exploiting the data as it is collected. In addition, existing sampling trajectory designs implicitly minimize $L_2$ error, which does not necessarily imply better perceptual image quality.

According to the approach of the present invention, an MRI undersampling trajectory is determined online and updated during the scan using reinforcement learning (RL). The image reconstruction technique is the environment, the reward is based upon an image metric, and the agent infers an updated sampling pattern for the next acquisition. The agent is statistically unbiased so it does not affect the results and insights that can be learned about the reconstruction technique and image metric.

A key feature of this approach is that it exploits real-time information to determine better sampling patterns, and also updates the sampling pattern as the scan progresses. As data is collected, the image can be better understood and the collected data is exploited in real-time to guide additional data collection.

The reinforcement learning technique incorporates scan data on a readout-by-readout basis, which makes it suitable for arbitrary MRI sampling trajectories, such as non-Cartesian and 2D, 3D, and higher dimensional trajectories, including time. By formulating the problem as a reinforcement learning problem, it makes finding a solution for online sampling trajectory optimization feasible. Also by formulating the problem as a reinforcement learning problem, the problem does not have to be end-to-end differentiable, enabling components such as the reward and environment to be non-differentiable.

In one aspect, the invention provides a method for performing a magnetic resonance imaging scan, the method comprising: performing an MRI acquisition using an undersampling pattern to produce undersampled k-space data; adding the undersampled k-space data to aggregate undersampled k-space data for the scan; reconstructing an image from the aggregate undersampled k-space data; updating the undersampling pattern from the reconstructed image and aggregate undersampled k-space data using a deep reinforcement learning technique defined by an environment, reward, and agent, where the environment comprises an MRI reconstruction technique, where the reward comprises an image quality metric, and where the agent comprises a deep convolutional neural network and fully connected layers; and repeating the previous steps to produce a final reconstructed MRI image for the scan.

Preferably, the MRI reconstruction technique produces a reconstructed image as output from undersampled k-space data as input. Examples include reconstruction techniques based on the Fourier transform, compressed sensing, and deep learning.

The image quality metric of the reward preferably uses an $L_2$ norm, $L_1$ norm, discriminators from trained generative adversarial networks, losses trained with semi-supervised techniques, and/or deep learning measures of image quality. The deep learning measures of image quality preferably are sharpness and/or signal-to-noise ratio.

The agent is preferably configured to have the reconstructed image and the aggregate undersampled k-space data as input and the updated undersampling pattern as output. The agent may be implemented, for example, as a three-layer residual convolutional neural network.

DETAILED DESCRIPTION OF THE INVENTION

Embodiments of the present invention provide MRI methods that use online deep reinforcement learning techniques for finding optimal undersampling patterns during a scan. The term "online" here means that the technique can process real-time data in a serial fashion as it becomes available.

Reinforcement learning in the context of this description is defined as a type of machine learning involving a software agent that takes actions in an environment to maximize a reward. In embodiments of this invention, the environment is an MRI reconstruction technique, with undersampled k-space as input and the reconstructed image as output. Reconstruction techniques may include, for example, algorithms based upon the Fourier transform, compressed sensing, and deep learning. The reward in embodiments of this invention is defined by an image quality metric on an MRI image. The tested metrics were based upon $L_2$ norm, $L_1$ norm, and metrics based upon deep learning, such as discriminators from trained generative adversarial networks and losses trained with semi-supervised techniques.

Figure 1A:
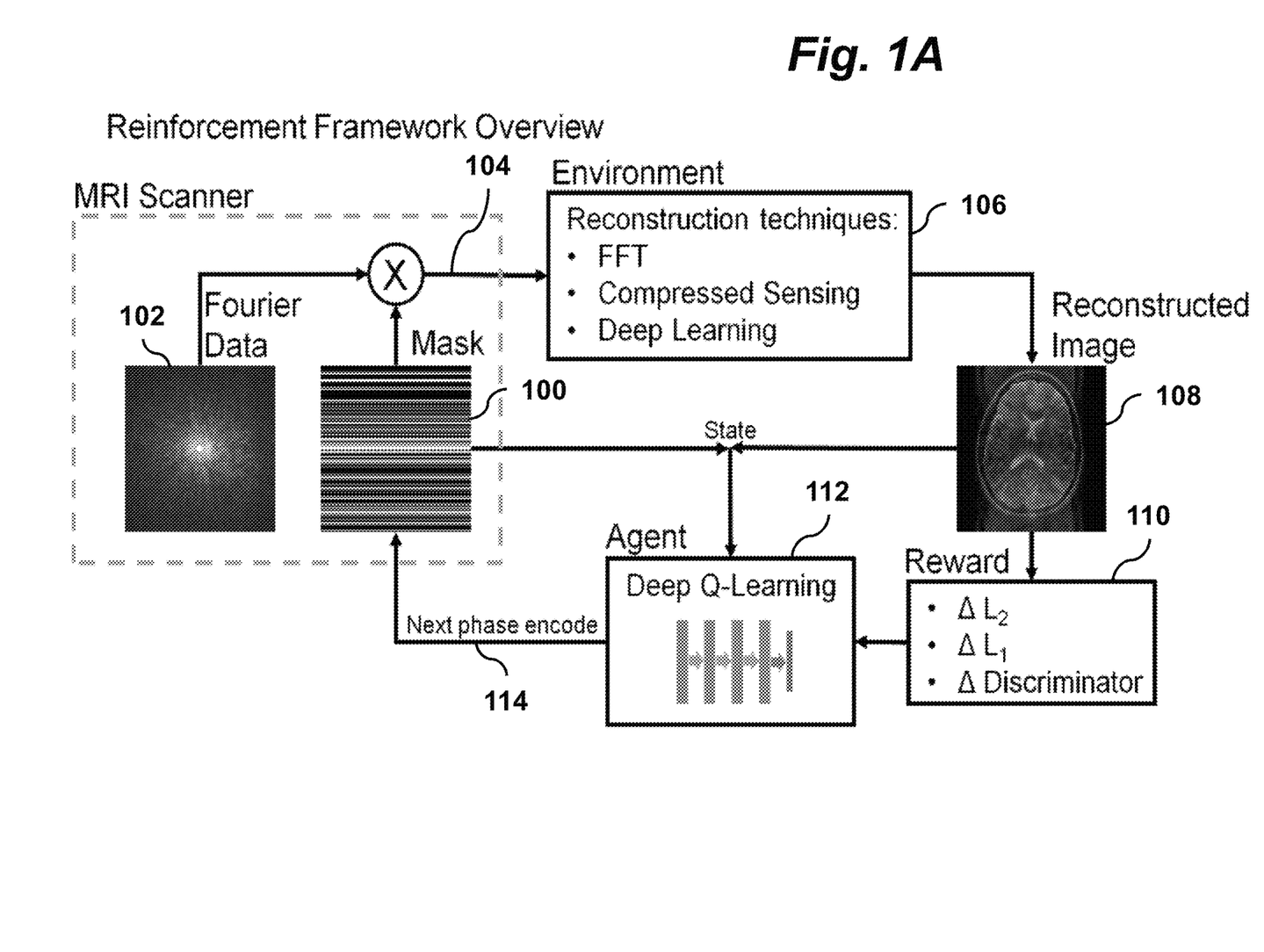
FIG. 1A is an overview of the reinforcement learning processing pipeline according to an embodiment of the invention.

FIG. 1A is an overview of the reinforcement learning processing pipeline according to an embodiment of the invention. During MRI acquisition, sampling pattern mask 100 is used for sampling k-space (Fourier domain) data 102 to produce acquired k-space data 104. An image 108 is reconstructed from the acquired k-space data 104 by the environment 106, which is an MRI image reconstruction technique. The image 108 is then evaluated by an image quality metric 110, which defines the reward. The reward, the reconstructed image, and the sampling mask are provided to the agent 112, which determines an updated mask/sampling pattern 114 for the next MRI acquisition in the scan.

Figure 2:
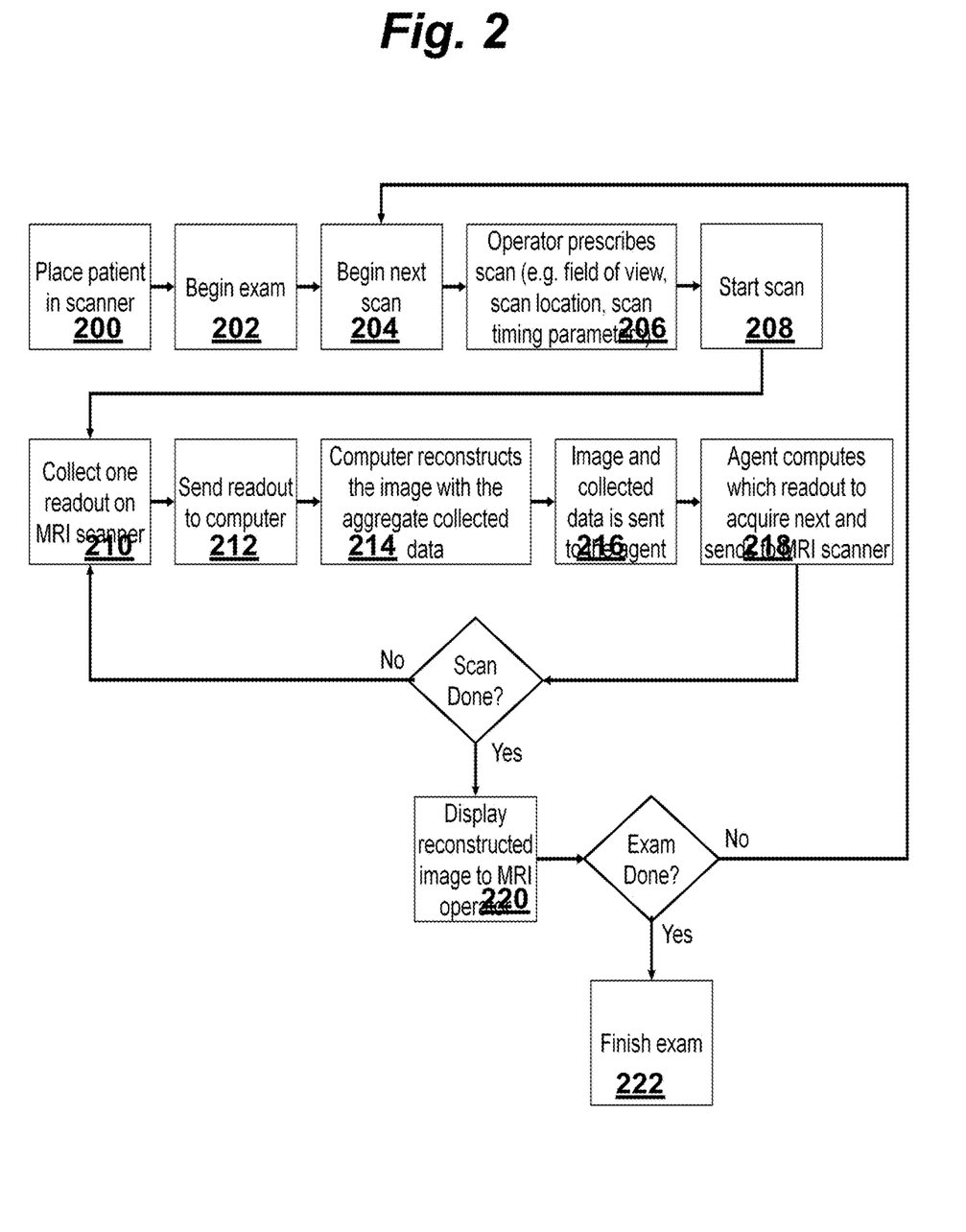
FIG. 2 is a flowchart of the steps for performing an MRI scan according to an embodiment of the invention.

FIG. 2 provides a flowchart of the steps for performing an MRI scan according to an embodiment of the invention. In step 200 a patient is placed in an MRI scanner, and the exam begins 202. A scan is started 204 and an operator prescribes scan parameters 206 which may include field-of-view, adjustment of the scan location, and adjustment of MRI scan-specific variables. The MRI apparatus then starts the scan data acquisition 208. The readout of k-space data acquired with a current sampling pattern is collected 210 and sent to the MRI computer 212 which then reconstructs an image from the aggregate collected data 214. The reconstructed image and aggregate data are passed through the reward and provided to the agent 216. Based upon the learned policy of the agent and the inputs, the agent computes an updated sampling pattern that will determine which readout to acquire next 218. If the scan is not yet completed, the process returns to step 210 to acquire k-space data using the updated sampling pattern. This repeats until the number of desired readouts is collected, or after a certain amount m of scan time, or until a certain minimum quality is achieved. When the scan is complete, the reconstructed image is stored and/or displayed 220. If the exam is not completed, the process returns to step 204 where a new scan is started, e.g., with different scan parameters. Otherwise, the exam is finished 222.

Figure 1B:
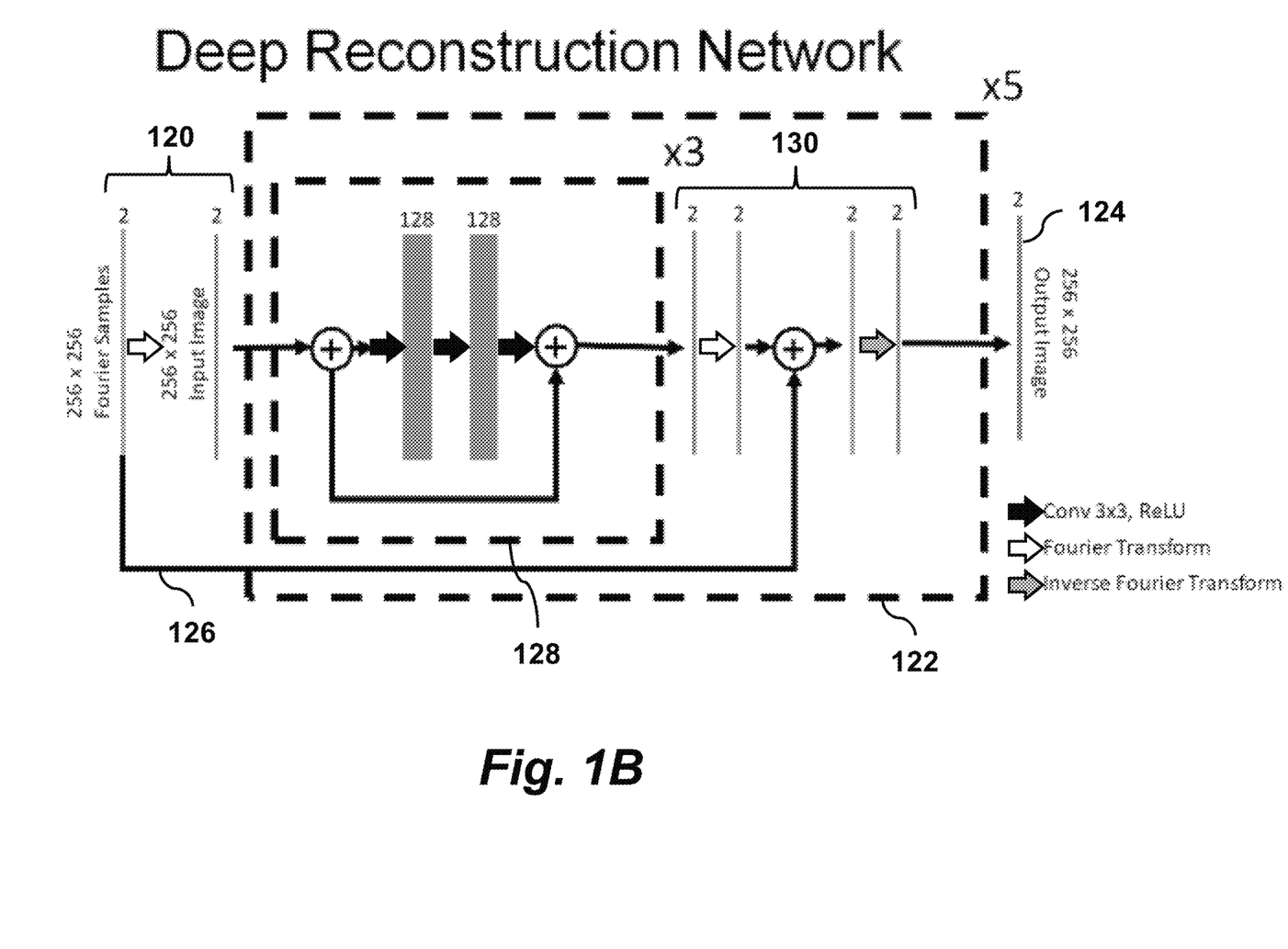
FIG. 1B is a schematic diagram illustrating the architecture of a deep reconstruction network according to an embodiment of the invention.

FIG. 1B is a schematic diagram illustrating the architecture of a deep reconstruction network (i.e., environment 106, FIG. 1A) according to an embodiment of the invention. The network has five repeated blocks 122 each of which includes three repeated residual network convolutional blocks 128 followed by a Fourier domain projection 130 for data consistency. The input 120 to the network is the k-space data with a Fourier transform applied to generate an image. Each layer of the residual block 128 has a feature depth of 128 and is a 3×3 convolution with rectified linear unit activation. The output of the final residual block goes to the set of Fourier domain projection layers 130 which transforms the data to the Fourier domain and transforms the data back to the image domain. The Fourier domain projection layers 130 have feature depth of 2 to represent the real and imaginary complex data. The Fourier projection from the input data is shown by 126. The output 124 is a reconstructed image.

The network 122 is preferably a generative adversarial network, where the generator for reconstructing the image is an unrolled optimization network trained with a supervised $L_1$ loss using randomly-weighted sampling patterns with 0%-100% sampled data on a different dataset than used for the reinforcement learning.

In other embodiments of the invention, the environment could be implemented using other image reconstruction techniques such as a Fourier transform or compressed sensing. For a compressed sensing reconstruction, $L_1$-ESPIRiT may be used with total variation regularization. For compressed sensing, a typical formulation is arg $\min_x \|Ax-y\|_2 + \lambda\|Tx\|_1$ where x is the reconstructed image, y is the collected data, A is some signal model transform (in the simplest case the Fourier transform), and T is some sparsifying transform such as wavelet or total variation. However, this implicitly has biases. A more general compressed sensing formulation is arg $$\min_x d(x, y) + \lambda R(x)$$

where d is some arbitrary distance function between the reconstructed image x and the collected data y, which could be an analytical function or a neural network. R(x) is an arbitrary regularizing term, which could be an analytical function or a neural network.

More generally, the input to the reconstruction network could be an image of any kind. The input could also be arbitrary collected data. k-space implies a Fourier relationship between the collected data and the final image but there are also non-Fourier data collection techniques and the reconstruction technique could address these as well. Furthermore, the reconstruction technique could accept any combination of k-space, image, and arbitrary collected data. As for output, the reconstruction technique could also output any combination of k-space, image, and arbitrary data. An example of arbitrary data output could be a vector in an embedding space.

Figure 1C:
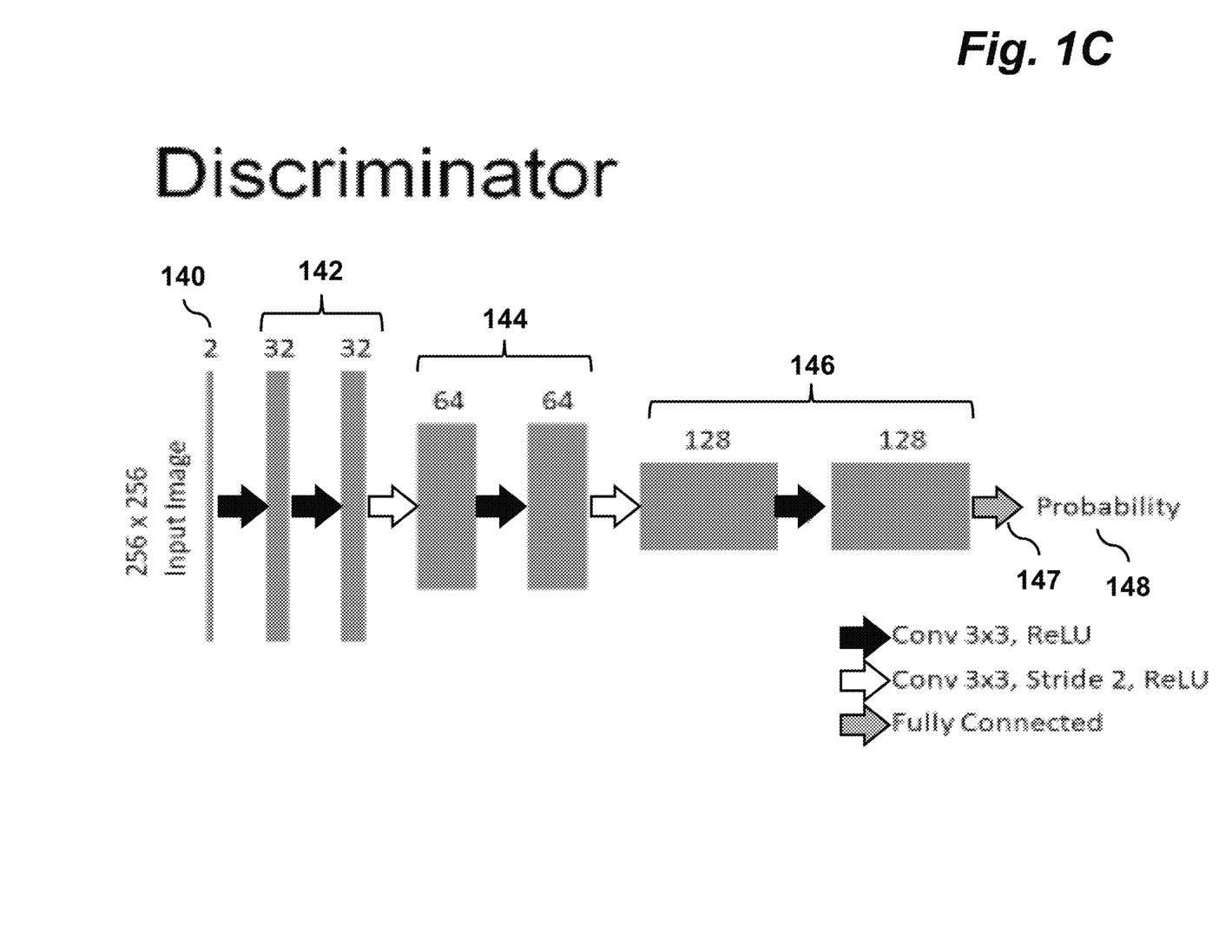
FIG. 1C is a schematic of a discriminator network architecture implementing the reward according to an embodiment of the invention.

FIG. 1C is a schematic of a discriminator network architecture implementing the reward (110, FIG. 1A) according to an embodiment of the invention. The discriminator is a six-layer convolutional network receiving an input image 140 and outputting a probability 148. The image first passes through two layers 142, which are 3×3 convolutions with rectified linear unit activations and feature depth of 32. The output of layers 142 is provided to layers 144 where it is convolved by a 3×33×3 convolution with stride 2 and feature depth 64, followed by a 3×3 convolution with stride 1 and feature depth 64. The output of layers 144 is then provided to layers 146 where it is convolved by a 3×3 convolution with stride 2 and feature depth 128 and then a 3×3 convolution with stride 1 and feature depth 128. The output probability 148 is computed by a fully connected layer 147 from the output of 146.

The probability output from the trained discriminators is an image metric. The reward is defined by subtracting the metric between the current acquisition step and the previous step. In this embodiment, the reward is the negative difference in probability between acquisition steps. To reward an earlier stopping condition for all metrics, we additionally added a −1% penalty to each sampling step.

Other embodiments of the invention may use different metrics. For example, the reward may be the difference in $L_2$ or $L_1$ metric between the current step and the previous step. More generally, the image quality metric could be any arbitrary metric. Also, the input to the reward can be image data, k-space data, or a combination of the two. An example of arbitrary data input could be a vector in an embedding space. The metric could also be implemented using any neural network.

Figure 1D:
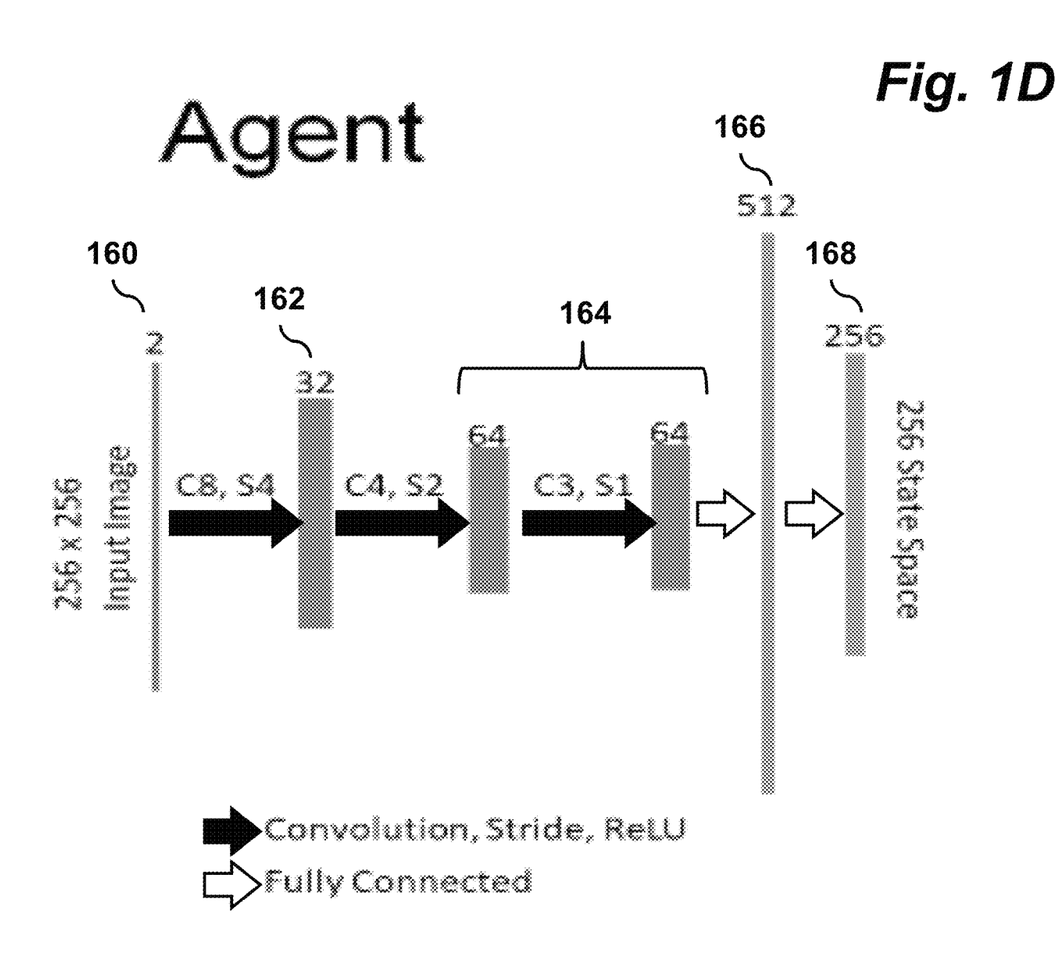
FIG. 1D is a schematic diagram of an agent network architecture for choosing the next optimal undersampling pattern according to an embodiment of the invention.

FIG. 1D is a schematic diagram of an agent network architecture (112, FIG. 1A) for choosing the next optimal undersampling pattern according to an embodiment of the invention. The agent network is a convolutional neural network with the complex-valued input 160 separated into real and complex values for a feature depth of 2. The input 160 is convolved by a 8×8 kernel with stride 4 and feature depth 32 in layer 162. The output of layer 162 is provided to layers 164 where it is convolved by a 4×4 kernel with stride 2 and feature depth 64 and then convolved by a 3×3 kernel with stride 1 and feature depth 64. The output of layers 164 is fed into a fully connected layer 166 with feature size 512. The output from first fully connected layer 166 is fed into a second fully connected layer 168 with feature size 256, where each feature corresponds to the size 256 state space. The action state space 168 has size 256, representing the 256 potential readouts to sample, and is encoded with is to represent already-sampled readouts. The state for the agent is a row vector of the current action space and the current reconstructed image.

The deep agent has convolutional neural networks and fully connected layers with and image domain input to decide which readout to acquire next, in real-time. In other embodiments, the inputs may be from both k-space and image domains The agent may be trained with various reinforcement learning methods. An agent may be trained with deep Q-learning methods with Rainbow, which includes double Q-learning, prioritized replay, dueling networks, multi-step learning, distributional reinforcement learning, and noisy nets for deep reinforcement learning, policy gradients for deep reinforcement learning, and residual networks for deep learning in general.

The agent can be online with respect to different time scales. The preferred embodiment has the agent learn a policy with respect to each readout. At one extreme, the learned policy could be online with respect to each sample, such that as each sample is collected, the agent is real-time deciding which next sample to collect. A readout is composed of many samples. The learned policy could also be online with respect to multiple readouts at a time, such that the agent decides which samples to collect in the next batch of readouts.

A deep Rainbow Q-learning agent may be trained to select the rows of the Fourier domain (Cartesian phase encodes) to sample. The network may be trained with the Bellman equation and discount factor γ=0.95. The action state may be a vector of rows already sampled and an image reconstructed with the currently sampled data. An ε-greedy approach may be used, selecting a random action with probability exponentially decaying from 0.9 to 0.05 over 1000 episodes. Experience replay may be used to de-correlate the experiences.

The agent may be trained by policy gradient methods to learn optimal policies for each combination of environment and reward. In commercial applications, each type of scan has its own type of reconstruction (environment) and potentially it could have its own image quality metric (reward). Thus, each scan would normally have its own agent. As for agent training method, all agents would normally be trained with the same method.

The techniques of the present invention were experimentally tested using a set of ten fully-sampled, 3D knee datasets from mridata.org for a total of 3,840 2D images cropped to 256×256. These central patches of 256×256 were taken from the axial slices for a total of 3,840 Fourier-domain datasets and corresponding 2D images.

To first verify performance, we constructed a toy dataset with each row in the Fourier domain having a constant, increasing value, such that a successful agent should learn to sample the rows sequentially. For this experiment, we used the inverse Fourier transform for the environment and $L_2$ for reward. We then trained the agent on real data, with all combinations of environments and rewards. With the $L_2$ reward specifically, Parseval's Theorem allows us to determine the actual optimal order of readouts. To evaluate the policy in general, we calculated the average number of readouts required to achieve less than 0.5% reward over 50 episodes.

Nine agents were trained, for every combination of environment and reward. As a benchmark to evaluate the learned policies, the average number of readouts required to achieve less than 0.5% reward was determined over 100 episodes. 0.5% reward was chosen as a stopping point, based upon initial results to achieve an undersampling factor of about two to three.

Figure 3A:
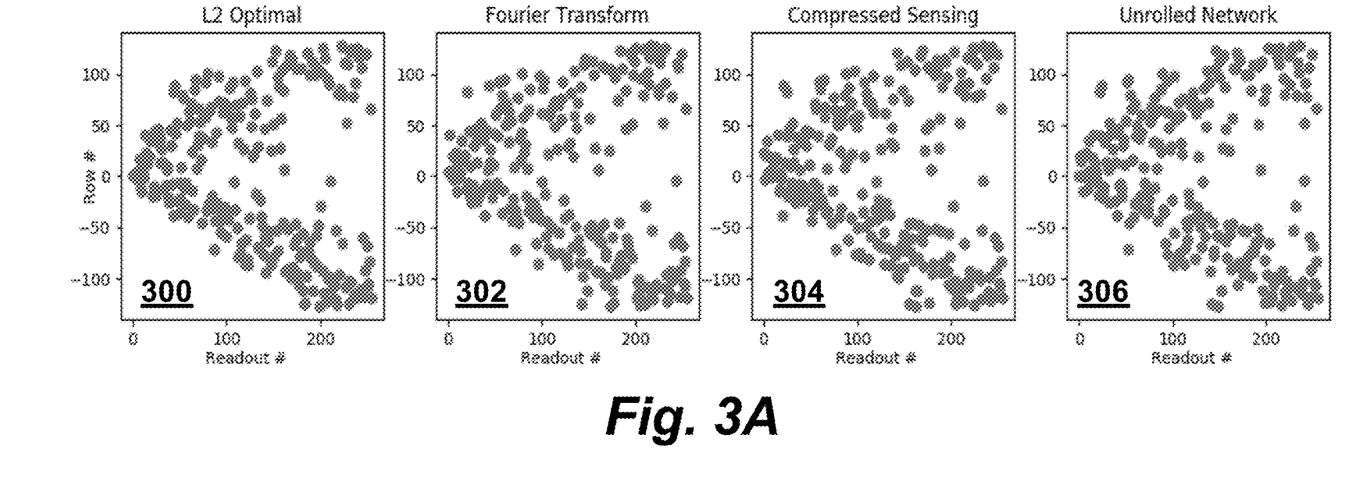
FIG. 3A show graphs of true $L_2$-optimal order of readouts and learned policy for order of readouts for different reconstruction environments.
Figure 3B:
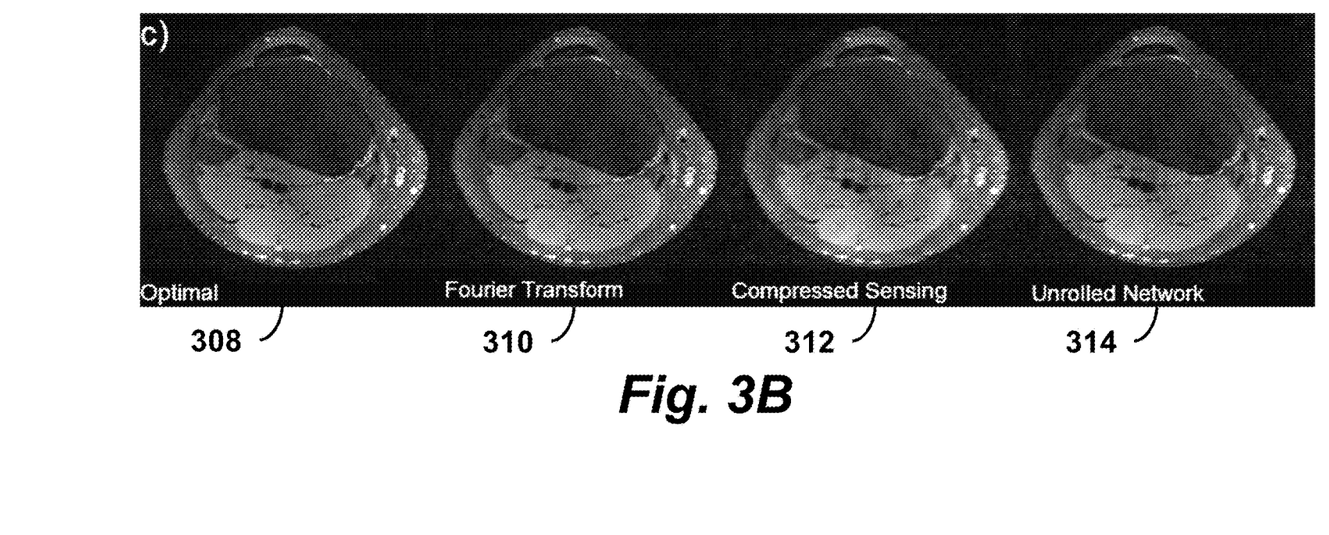
FIG. 3B shows reconstructed undersampled images with 0.5% $L_2$ reward for different reconstruction environments.
Figure 4A:
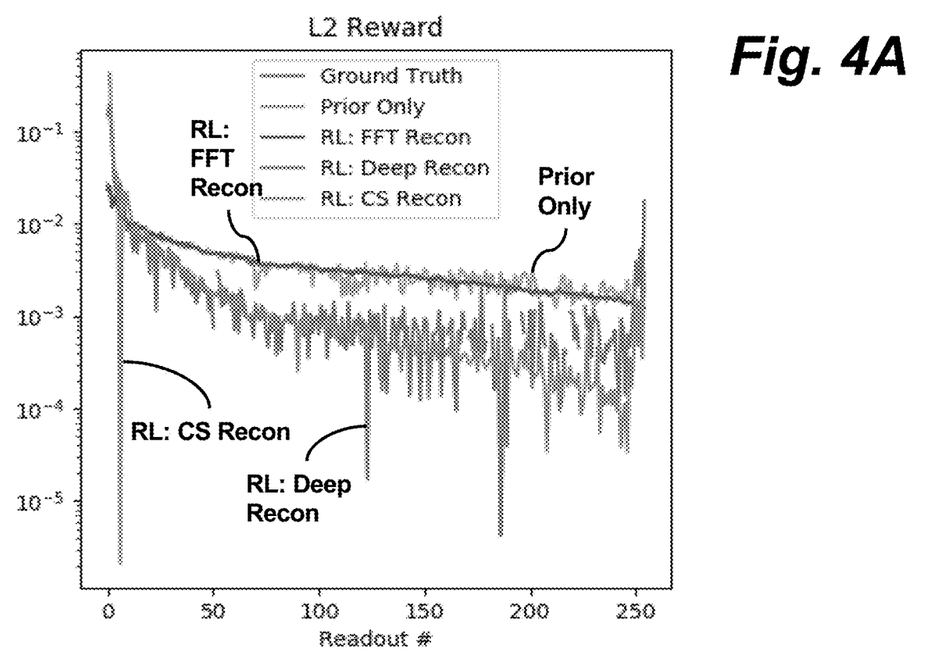
FIG. 4A is a graph of the $L_2$ reward earned for different reconstruction environments.
Figure 4B:
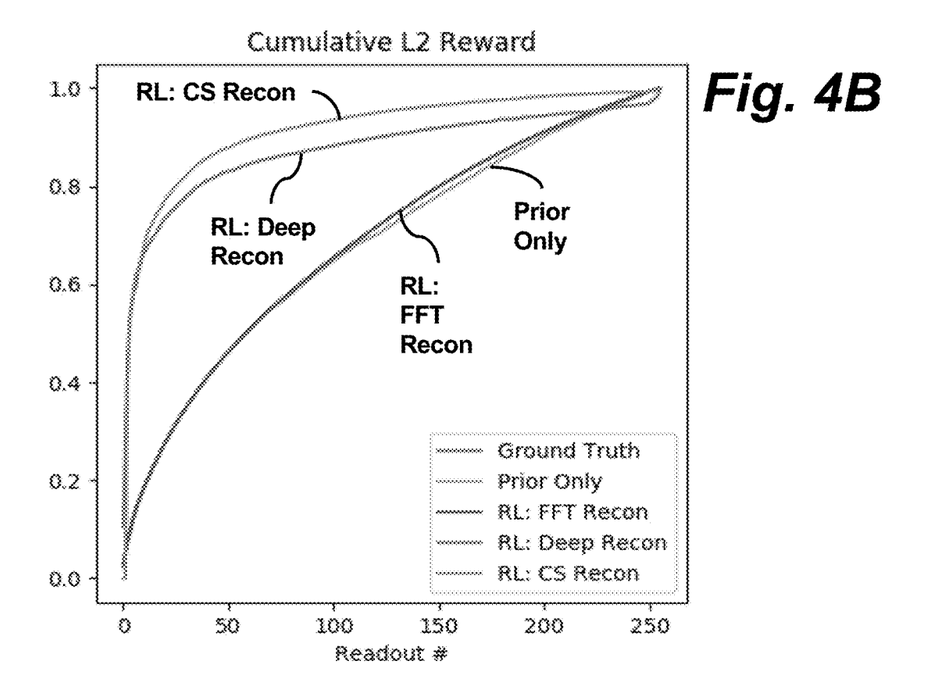
FIG. 4B is a graph of the cumulative $L_2$ reward for different reconstruction techniques.

FIGS. 3A-B show the learned policy and FIG. 4A-B show the reward per readout and cumulative reward as a function of policy. FIG. 3A show graphs of true $L_2$-optimal order of readouts and learned policy for order of readouts as a function of reconstruction environment: $L_2$ optimal 300, Fourier transform 302, compressed sensing 304, and unrolled network 306. FIG. 3B shows corresponding reconstructed undersampled images with 0.5% $L_2$ reward for $L_2$ optimal 308, Fourier transform 310, compressed sensing 312, and unrolled network 314.

FIG. 4A-B show graphs of learned policies applied for a single image. FIG. 4A shows the $L_2$ reward earned for different reconstruction environments. FIG. 4B shows the cumulative $L_2$ reward for different reconstruction techniques. In both FIG. 4A and FIG. 4B, the ground truth line is substantially identical with the FFT reconstruction. The "Prior only" uses prior information, without online information. The policy using only prior-learned information was less consistent in choosing the best sample. Thus, in this instance where the solution is known, the reinforcement learning agent using online information outperformed the agent using only prior information.

Both compressed sensing and deep reconstructions acquired reward more quickly, echoing the results in FIG. 3A-B. The deep reconstruction acquired reward more slowly than the compressed sensing likely because the deep reconstruction was trained with an $L_1$ loss.

Figure 5:
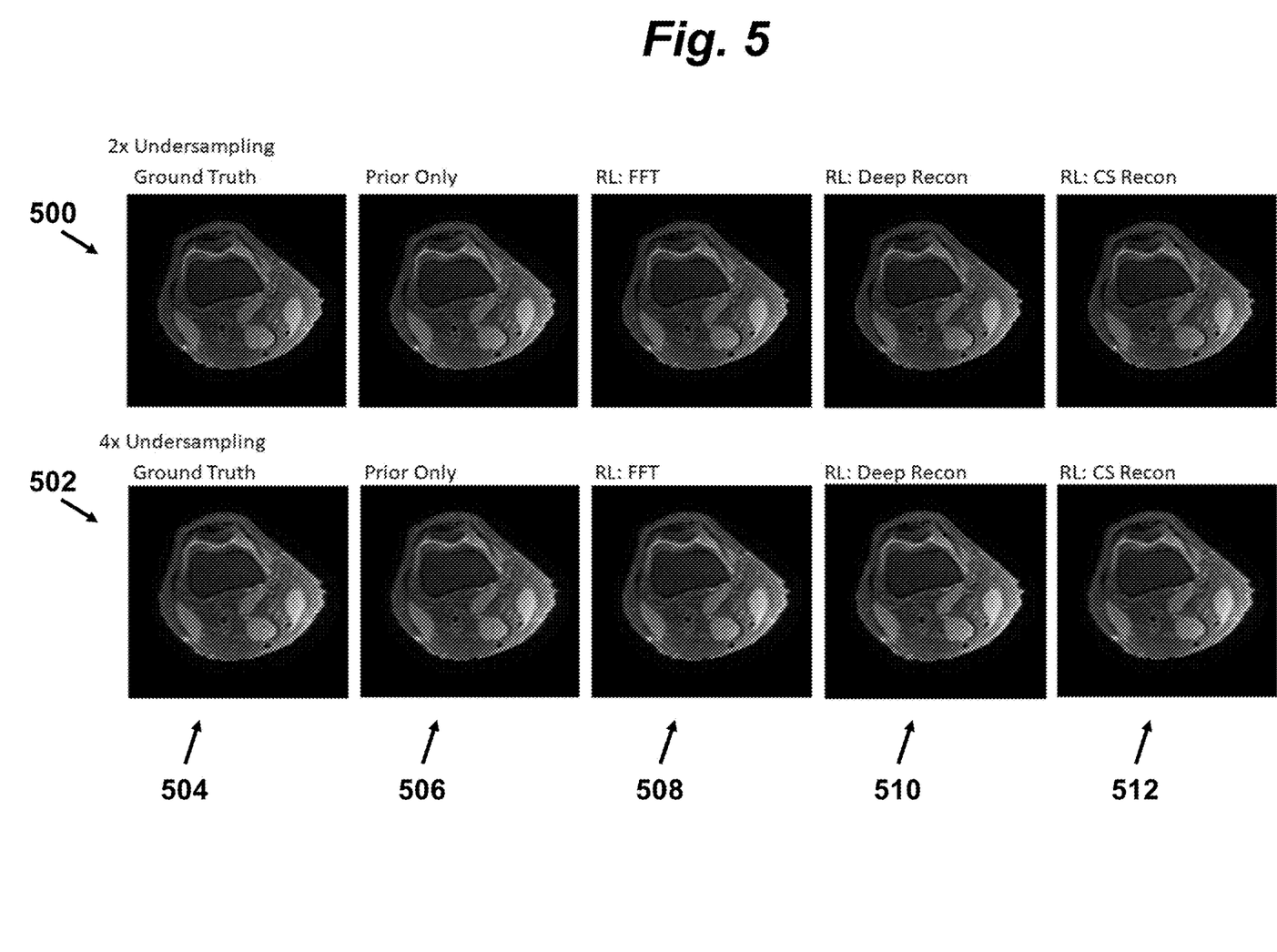
FIG. 5 is a grid of reconstructed images with optimal 2× and 4× undersampling trajectories for $L_2$ reward.

FIG. 5 shows a grid of reconstructed images with optimal 2× (row 500) and 4× (row 502) undersampling trajectories for $L_2$ reward. The columns 504, 506, 508, 510, 512 correspond to the ground truth, prior only, FFT, deep reconstruction, and compressed sensing reconstruction, respectively. All the images look similar because the $L_2$ reward only approximately captures human-perceptual visual image quality.

Similar to the optimal policy, the learned policies of all reconstruction environments sample the center of the Fourier domain first, before sampling higher spectral components. The corresponding images, sampled until 0.5% $L_2$ reward, are shown in FIG. 3B.

TABLE 1 shows the average number of readouts to achieve less than 0.5% reward as a function of reconstruction. Compressed sensing and the deep reconstruction require fewer readouts than the Fourier transform reconstruction because these techniques infer the image based upon on priors.

From the results in TABLE 1, the unrolled network requires significantly fewer readouts than compressed sensing to achieve the same reward, which makes sense because the network has learned the prior distribution. Also interestingly, compressed sensing requires more samples than the Fourier Transform to achieve a 0.5% reward with the discriminator. This may be because the discriminator is unfamiliar with the image artifacts that compressed sensing produces.

The compressed sensing and deep reconstruction techniques required fewer readouts than the Fourier transform reconstruction for the $L_2$ and $L_1$ rewards. This makes sense because the former two techniques are designed to infer data from undersampled raw data.

TABLE 1

| Reward | Fourier Transform | Compressed Sensing | Deep Reconstruction |
| --- | --- | --- | --- |
| $L_2$ | 140.4 | 89.8 | 82.7 |
| $L_1$ | 119.1 | 94.8 | 55.7 |
| Discriminator | 112.0 | 120.9 | 68.4 |

The reinforcement learning framework provides nearly optimal results. The results highlight the inability of the $L_2$ reward to capture image quality. This provides motivation for the development of image quality metrics better aligned with diagnostic quality, which could then be addressed by the reinforcement learning framework.

The framework formulation can accommodate non-Cartesian and higher dimensional trajectories as well as 2D Cartesian trajectories. Adapting this technique to higher dimensions is straightforward to implement with additional computational and storage resources. However, it would be expected to require greater effort to stably train the agent, as the action space exponentially grows in size.

The way the reinforcement learning has been defined makes it compatible with arbitrary MRI reconstruction techniques and image quality metrics, making it valuable for future deep learning reconstruction techniques and deep learning image quality metrics. Additionally, the present technique is general enough to account for other considerations such as dynamic imaging and artifacts from m sources such as motion.

Furthermore, the present technique does not introduce bias or require assumptions to learn the policy. Given the environment and reward, the agent learns an optimal policy, guided by the biases and assumptions introduced by the environment and reward. For example, compressed sensing minimizes an $L_2$ data-consistency term and deep learning networks usually minimize a supervised $L_1$ loss. As new techniques emerge, the traditional intuition to sample the center may not be as pronounced. This is especially plausible with the development of semi-supervised and unsupervised techniques for training deep learning reconstruction algorithms and deep-learning based image quality metrics. In these cases, the results of this reinforcement learning framework may not necessarily follow the conventional intuition and the resultant sampling patterns may help elucidate the behavior of these networks.

The invention claimed is:

1. A method for performing a magnetic resonance imaging scan, the method comprising:
   a) performing an MRI acquisition using an undersampling pattern to produce undersampled k-space data;
   b) adding the undersampled k-space data to aggregate undersampled k-space data for the scan;
   c) reconstructing an image from the aggregate undersampled k-space data;
   d) updating the undersampling pattern from the reconstructed image and aggregate undersampled k-space data using a deep reinforcement learning technique defined by an environment, reward, and agent, where the environment comprises an MRI reconstruction technique, where the reward comprises an image quality metric, and where the agent comprises a deep convolutional neural network and fully connected layers;
   e) repeating steps (a), (b), (c), and (d) to produce a final reconstructed MRI image for the scan.

2. The method of claim 1 where the MRI reconstruction technique produces a reconstructed image as output from undersampled k-space data as input.

3. The method of claim 1 where the image quality metric of the reward uses an $L_2$ norm, $L_1$ norm, discriminators from trained generative adversarial networks, losses trained with semi-supervised techniques, and/or deep learning measures of image quality.

4. The method of claim 3 where the deep learning measures of image quality are sharpness and/or signal-to-noise ratio.

5. The method of claim 1 where the agent is configured to have the reconstructed image and the aggregate undersampled k-space data as input and the updated undersampling pattern as output.

6. The method of claim 1 where the agent is implemented as a three-layer residual convolutional neural network.

* * * * *